United States Patent
Koseoglu et al.

(10) Patent No.: US 10,527,546 B2
(45) Date of Patent: Jan. 7, 2020

(54) CHARACTERIZING CRUDE OIL USING LASER INDUCED ULTRAVIOLET FLUORESCENCE SPECTROSCOPY

(71) Applicant: Saudi Arabian Oil Company, Dhahran (SA)

(72) Inventors: Omer Refa Koseoglu, Dhahran (SA); Adnan Al-Hajji, Dammam (SA); Ezzat Hegazi, Ontario (CA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/179,317

(22) Filed: Jun. 10, 2016

(65) Prior Publication Data
US 2016/0363533 A1      Dec. 15, 2016

Related U.S. Application Data

(60) Provisional application No. 62/173,558, filed on Jun. 10, 2015.

(51) Int. Cl.
*G01N 21/64* (2006.01)
*G01N 33/28* (2006.01)
(Continued)

(52) U.S. Cl.
CPC .............. *G01N 21/64* (2013.01); *G01N 9/36* (2013.01); *G01N 21/33* (2013.01);
(Continued)

(58) Field of Classification Search
CPC ...... G01N 21/64; G01N 21/6402; G01N 9/36; G01N 33/28
See application file for complete search history.

(56) References Cited

U.S. PATENT DOCUMENTS

| | | | | |
|---|---|---|---|---|
| 5,475,612 A | * | 12/1995 | Espinosa | G01N 21/359 250/339.07 |
| 5,691,809 A | | 11/1997 | Tackett et al. | |

(Continued)

FOREIGN PATENT DOCUMENTS

| | | |
|---|---|---|
| DE | 10239028 A1 | 3/2003 |
| WO | 2009080049 A1 | 7/2009 |
| WO | 2013023299 A1 | 2/2013 |

OTHER PUBLICATIONS

Martin et al., "Direct Push Site Characterization of NAPL with Laser-Induced Fluorescence (LIF)", Dakota Technologies, 2008 North American Environmental Field Conference & Exposition (Jan. 16, 2008): pp. 1-69 (https://clu-in.org/download/char/lif/Dakota-Technologies-LIF-Workshop.pdf).*

(Continued)

*Primary Examiner* — Michele Fan
(74) *Attorney, Agent, or Firm* — Bracewell LLP; Constance G. Rhebergen; Brian H. Tompkins

(57) ABSTRACT

Embodiments of the present disclosure describe a method for determining a property of an uncharacterized crude oil sample using a polynomial equation correlating the property to a spectrum index and density of crude oil. The polynomial equation may include constants determined using a data fitting method and a data base of spectral data, density data, and standard properties data of a plurality of crude oils.

15 Claims, 3 Drawing Sheets

(51) Int. Cl.
*G01N 9/36* (2006.01)
*G01N 21/33* (2006.01)

(52) U.S. Cl.
CPC ......... *G01N 21/6402* (2013.01); *G01N 33/28* (2013.01); *G01N 33/2823* (2013.01); *G01N 2201/06113* (2013.01); *G01N 2201/12* (2013.01)

(56) References Cited

U.S. PATENT DOCUMENTS

| | | | |
|---|---|---|---|
| 6,272,376 | B1 | 8/2001 | Marcu et al. |
| 6,275,775 | B1* | 8/2001 | Baco ................. E21B 49/00 436/161 |
| 6,633,043 | B2 | 10/2003 | Hegazi et al. |
| 7,595,876 | B2 | 9/2009 | DiFoggio |
| 2002/0158211 | A1 | 10/2002 | Gillispie |
| 2003/0141459 | A1 | 7/2003 | Hegazi et al. |
| 2003/0195708 | A1* | 10/2003 | Brown ................. G01N 21/35 702/22 |
| 2007/0013911 | A1 | 1/2007 | DiFoggio |
| 2007/0267327 | A1* | 11/2007 | Boakye ................. C10G 27/00 208/253 |
| 2008/0035858 | A1 | 2/2008 | Hegazi |
| 2008/0253426 | A1* | 10/2008 | Voelkening ............ G01N 25/08 374/27 |
| 2012/0043477 | A1 | 2/2012 | Hegazi et al. |
| 2012/0132568 | A1* | 5/2012 | Foulonneau ......... C10G 19/073 208/263 |
| 2013/0319908 | A1* | 12/2013 | Halais ...................... C10G 1/00 208/14 |
| 2014/0156241 | A1* | 6/2014 | Kumar ............... G01N 33/2823 703/6 |
| 2014/0373649 | A1* | 12/2014 | Harrell .................. G01N 17/00 73/866 |
| 2015/0106028 | A1* | 4/2015 | Koseoglu ........... G01N 33/2823 702/23 |
| 2015/0106031 | A1* | 4/2015 | Koseoglu ........... G01N 21/3577 702/24 |
| 2015/0112611 | A1* | 4/2015 | Koseoglu ............... C10G 35/00 702/25 |

OTHER PUBLICATIONS

Germain, "Interpreting LIF Waveforms", Dakota Technologies, LIF Line Newsletter (Feb. 2013): pp. 1-6(http://www.dakotatechnologies.com/info/newsletters/article/2013/07/12/interpreting-lif-waveforms).*

Knowles et al., "Laser induced fluorescence spectroscopy for in-situ detection fo petroleum contamination", Navy (1996): pp. 1-5 (http://www.dtic.mil/dtic/tr/fulltext/u2/a348854.pdf).*

Ali et al., "Determination of Optimal Cut Point Temperatures at Crude Distillation Unit using the Taguchi Method", International Journal of Engineering & Technology, 12 (2012): pp. 36-46.*

International Search Report and Written Opinion for International Application No. PCT/US2016/036929; International filing date Jun. 10, 2016; Report dated Sep. 13, 2016.

\* cited by examiner

CHARACTERIZING CRUDE OIL USING LASER INDUCED ULTRAVIOLET FLUORESCENCE SPECTROSCOPY

FIELD

The disclosure herein relates to characterization of crude oil. More specifically, the disclosure herein relates to the use of spectroscopic and physicochemical measurements for determining selected chemical and physical properties of crude oils and fractions of crude oils.

BACKGROUND

Efficient production and refining of crude oil is essential for meeting certain global energy needs. The efficiency may be impacted by the wide variation of the composition and properties of various crude oils. Crude oils obtained via downhole drilling and recovery operations may provide crude oils comprised of thousands of hydrocarbon species of variable properties and proportions. These hydrocarbon species may include gasoline, diesel, jet fuel, polymer feedstocks, and other commercially important carbonaceous products. The analysis and characterization of the various hydrocarbon fractions typically involves time intensive techniques and assays including distillation and fractionation of relatively large quantities of crude oil, with the resulting distilled and/or fractionated hydrocarbons subjected to individual analytical and physicochemical analyses. These procedures may require up to 20 liters of crude oil as a starting amount. While these procedures are well-established and widely understood by the skilled artisans of the oil industry, whole crude oil sample analyses on smaller sample sizes in the absence of chemical separations techniques may be advantageous since this may provide a procedure to characterize small samples much more rapidly.

SUMMARY

Various embodiments disclosed herein may relate to a method for determining a property of a crude oil sample using a correlation of the property to a spectrum index and a density. In various embodiments, the method may include obtaining a value of a property of a plurality of crude oils using a standard analysis method. In various embodiments, the method further may include obtaining a value of a density of the plurality of crude oils. In various embodiments, the method further may include obtaining data sets of scatter spectra for the plurality of crude oils. In various embodiments, the method further may include calculating spectra indexes from the data sets of the scatter spectra of the plurality of crude oils. In various embodiments, the method further may include determining constants of a polynomial equation for the property, wherein the polynomial equation is a function of density and spectrum index of an uncharacterized crude oil, wherein a number of constants of the polynomial equation is equal to or less than the number of the plurality of crude oils, wherein the constants are determined using a fitting method to fit the value of the property of the plurality of crude oils to a calculated value from the polynomial equation. In various embodiments, the method further may include obtaining a scatter spectrum and a density of the uncharacterized crude oil sample and calculating a spectrum index and a value of the property of the uncharacterized crude oil sample using the polynomial equation, wherein the uncharacterized crude oil sample is not one of the plurality of crude oils.

In various embodiments, the property may be selected from the group consisting of cetane number, pour point, cloud point, and aniline point of a gas oil fraction, octane number of a naphtha fraction, and aromatic content of a gas oil fraction crude oil. In various embodiments, the gas oil fraction may have a boiling point range of approximately 180 to 370° C. In various embodiments, the naphtha fraction may have a boiling point of approximately 36 to 180° C. In various embodiments, the cetane number may be obtained using ASTM D613. In various embodiments, the pour point may be obtained using ASTM D7346. In various embodiments, the cloud point may be obtained using ASTM D2500. In various embodiments, the aniline point may be obtained using ASTM D611. In various embodiments, the octane number may be obtained using at least one of a test for a motor octane, a research octane, and combinations thereof, wherein a value for the motor octane is obtain using ASTM D2700 and a value for the research octane is obtained using ASTM D2699. In various embodiments, the aromatic content may be obtained using any ASTM test or other suitable test. In various embodiments, the density may be obtained using ASTM D5002.

In various embodiments, the scatter spectra may be obtained using a laser induced ultraviolet (UV) fluorescence spectrometer. In various embodiments, the spectra indexes from the scatter spectra of the plurality of crude oils may be calculated from an indicative value (IN) of an area under a plot of fluorescence intensity (FI) versus a wavelength of UV light detected by a UV detector of the laser induced UV fluorescence spectrometer. In various embodiments, the IN of an area may be calculated via $$IN = \sum_{\omega=\omega 1}^{\omega 2} \frac{FI_\omega}{10^6},$$

$\omega$ is wavelength of UV light, $\omega 1$ is a beginning wavelength of UV light, and $\omega 2$ is an ending wavelength of UV light, wherein the beginning and ending wavelength of UV light may be selected to be at FI values greater than background noise of FI. In various embodiments, $\omega$ may be incremented by one wavelength in the summation equation.

In various embodiments, the IN of an area may be calculated by integrating the area under the plot of FI versus a wavelength of UV light detected by the UV detector of the laser induced UV fluorescence spectrometer from a beginning wavelength of UV light to an ending wavelength of UV light, wherein the beginning and ending wavelengths of UV light may be selected to be at FI values greater than background noise of the FI. In various embodiments, the scatter spectra may be obtained using a spectroscopy method selected from the group consisting of absorption spectroscopy, Raman spectroscopy, resonance Raman spectroscopy, transmission spectroscopy, ultraviolet-visible reflectance spectroscopy, and combinations thereof. In various embodiments, the polynomial equation may be $PROP = K + X_1*D + X_2*D^2 + X_3*D^3 + X_4*IN + X_5*IN^2 + X_6*IN^3 + X_7*D*IN$, wherein PROP is a calculated value of the property, K and $X_i$ are constants specific to the respective property where i=1-7, D is density, and IN is spectrum index.

BRIEF DESCRIPTION OF THE DRAWINGS

Embodiments will be readily understood by the following detailed description in conjunction with the accompanying drawings. To facilitate this description, like reference numerals designate like structural elements or procedures in a method. Embodiments are illustrated by way of example and not by way of limitation in the figures of the accompanying drawings.

DETAILED DESCRIPTION

Figure 1:
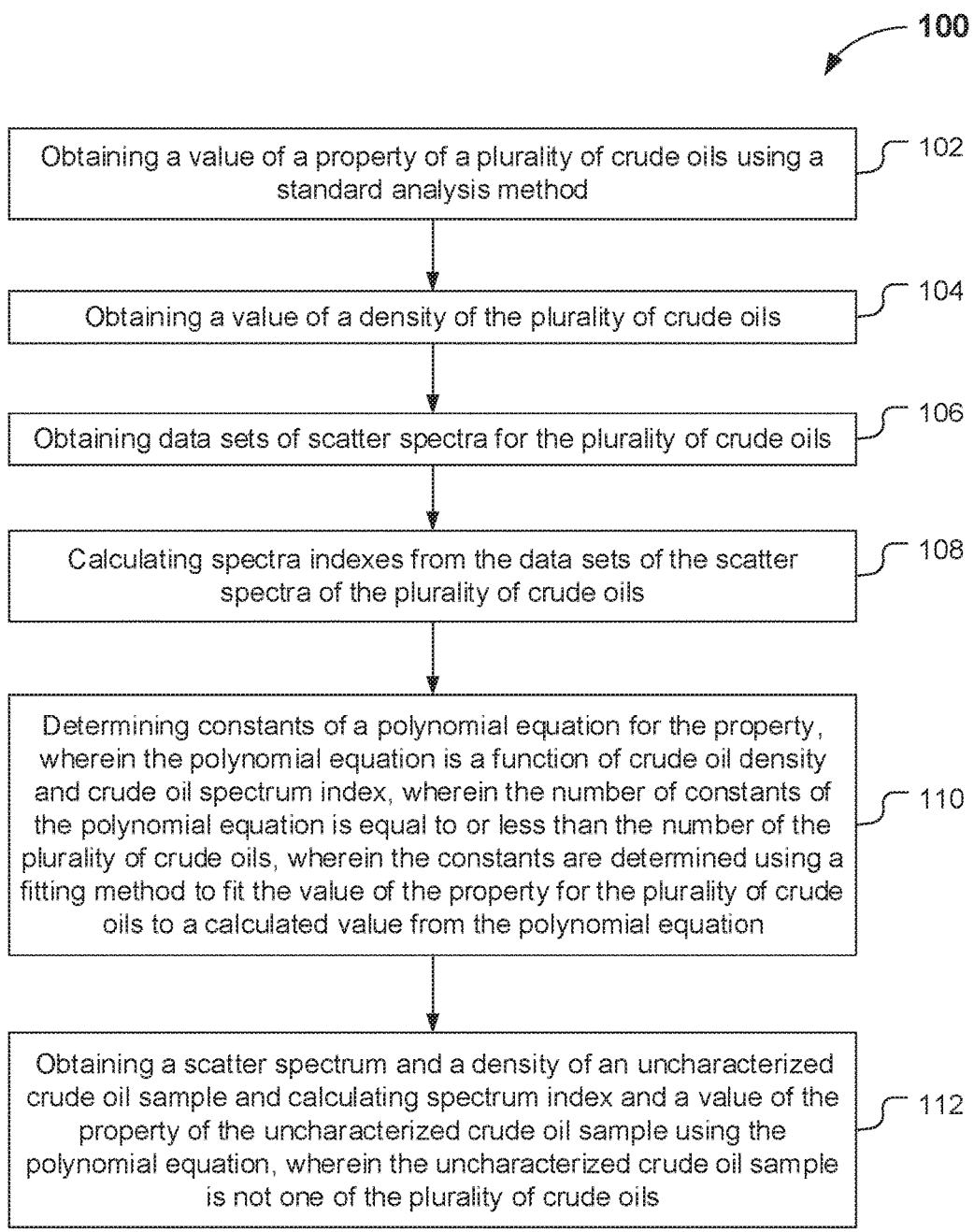
FIG. 1 schematically illustrates a method for determining a property of a crude oil sample using a correlation of the property to a spectrum index and a density, in accordance with various embodiments.

Embodiments of the present disclosure describe methods for characterizing crude oil and fractions of a crude oil using data from scatter spectroscopy, crude oil density data, and standard testing data to develop correlations of selected properties to a spectroscopy index and crude oil density. These correlations may be used to predict values for uncharacterized crude oils. Further embodiments may be described and disclosed herein.

In the following description, numerous specific details are set forth in order to provide a thorough understanding of the various embodiments. In other instances, well-known processes and methods may not been described in particular detail in order not to unnecessarily obscure the embodiments described herein. Additionally, illustrations of embodiments herein may omit certain features and/or details in order to not obscure the embodiments described herein.

In the following detailed description, reference is made to the accompanying drawings that form a part hereof, wherein like numerals designate like parts throughout, and in which is shown by way of illustration embodiments in which the subject matter of the present disclosure may be practiced. Other embodiments may be utilized, and logical changes may be made without departing from the scope of the present disclosure. Therefore, the following detailed description is not to be taken in a limiting sense.

The description may use the phrases "in various embodiments," "in various embodiments," "in an embodiment," or "in embodiments," which may each refer to one or more of the same or different embodiments. Furthermore, the terms "comprising," "including," "having," and the like, as used with respect to embodiments of the present disclosure, are synonymous.

The term "cetane number", alternatively referred to as a "cetane point", "cetane rating" or "cetane index", refers to the combustion rate or process for a diesel fuel or related hydrocarbons generally in the $C_{10}$ to $C_{15}$ range. A cetane number corresponds to a value between 0 (the reference value for methylnaphthalene) and 100 (the reference value for cetane (hexadecane)). A typical CN for diesel fuel may be in the range of about 40 to about 60. A CN may be determine for a hydrocarbon fraction boiling between 150 and 400° C. or a sub-fraction within that temperature range.

The term "pour point" refers to the temperature of a liquid or fluid below which the liquid or fluid is incapable of flowing. Pour point may also be regarded as the temperature at which a liquid or fluid becomes "semi-solid". For example, at a pour point of a hydrocarbon (such as crude oil or a fraction of crude oil for example), the hydrocarbon may appear plasticized or appear in a plastic compositional form such that the hydrocarbon is extremely viscous and does not readily flow.

The term "cloud point" refers to the temperature of a hydrocarbon fraction such as a diesel, wax, asphaltene, resin, and/or combinations thereof below which a substituent of the fraction exhibits a cloudy or opaque appearance. The substituent may be referred to as a wax or wax-like substituent. A cloud point may alternatively be referred to as a wax appearance temperature or a wax precipitation temperature.

The term "aniline point" refers to the minimum temperature at which a defined volume of a liquid hydrocarbon, such as crude oil or a fraction thereof, is miscible with an equal volume of aniline, also known as aminobenzene and phenylamine. In certain assays well known in the relevant art, one or more additional chemicals, such as n-heptane, may be further added to the aniline/liquid hydrocarbon mixture.

The terms "octane number" and "octane rating" refer to a figure quantitatively describing the performance properties of a combustible hydrocarbon species or combustible fuel such as petroleum, crude oil, kerosene, and related naphtha derived distillates and condensates. The octane number is often determined using standard assays well known in the art such as the ASTM International D2699 or D2700 standard test methods and may be expressed as a measure of a fuel's ability to prevent detonation in a spark ignition engine. This value is often determined using a standard single cylinder using a variable-compression-ratio engine and compared or benchmarked using primary reference fuels. An octane number may be alternatively expressed as a research octane number, which is often used as an expression of an octane number under mild engine operating conditions. In addition, a motor octane number may be used to express an octane number for an engine operating under more severe operating conditions. A related value known as the antiknock index is often associated with the research octane number and/or motor octane number in commercial applications or as required by local law. The antiknock index is determined by calculating the arithmetic average of the research octane number and the motor octane number, i.e. (R+M)/2. The antiknock index may be used to approximate a "road octane number", which is a measure of how an average car performs in response to its (hydrocarbon) fuel source.

The terms "laser-induced fluorescence spectroscopy", "LED induced fluorescence", and "LIF" refer to a spectroscopic method where a sample is photochemically excited using a pulsed or continuous laser radiation source to produce time and wavelength resolved fluorescence spectra of the sample. In various embodiments, the radiation source may be an ultraviolet radiation source. In various embodiments, laser-induced fluorescence spectroscopy may be used to determine the concentration of hydrocarbon species and/or non-hydrocarbon contaminants for evaluating the properties of a crude oil sample. In various embodiments, laser-induced fluorescence spectroscopy may be used to generate two-dimensional and/or three-dimensional images of a crude oil sample. While not limiting the breadth or scope of the various embodiments herein, the use of laser-induced fluorescence spectroscopy for the characterization of liquid hydrocarbons, such as crude oils, has previously been described in U.S. Pat. No. 6,633,043 to Hegazi et al.

The methods disclosed herein address several well-known problems that are frequently encountered in the oil industry related to the need to characterize variable crude oils and fractions thereof. For instance, the physical and chemical properties of crude oils can vary significantly between geographic regions and even between adjacent or relatively proximal oil fields. Accordingly, the physical and chemical properties need to be determined for each of the different crude oils in order to optimize production of the crude oil and products made therefrom. The methods disclosed herein address the challenges associated with characterizing the various crude oils and fractions thereof by advantageously utilizing spectroscopic techniques and physicochemical measurements. In various embodiments, these methods may be used to accurately determine properties of crude oil and selected fractions thereof. In various embodiments, hydrocarbon constituents may be characterized, where the constituents may include but are not limited to alkanes, alkenes, paraffins, cycloparaffins, naphthenes, aromatics, and polynuclear aromatic hydrocarbons. In various embodiments, the methods disclosed herein may be used to characterize non-hydrocarbon constituents of crude oil including but not limited to sulfur, nitrogen, nickel, and vanadium. In addition, the methods disclosed herein may allow for the rapid assessment of the chemical composition and quantitative analysis of a crude oil sample or fraction of interest as compared to traditional assays and techniques well known to the skilled artisan.

A crude oil assay is a traditional method of determining the characteristics of crude oils for benchmarking purposes. For instance, a crude oil assay often involves securing several liters of a crude oil and subjecting the crude oil to true boiling point (TBP) distillation and/or fractionation for determining the boiling point fractions present in the crude oil. The crude oil distillation and/or fractionation may be carried out using any standard technique known to the skilled artisan, such as the American Standard Testing Association (ASTM) Method D 2892 for crude oil distillates. Common hydrocarbon fractions of crude oil and the nominal boiling points thereof are provided in Table 1. Table 2 provides typical yields, composition, physical and indicative properties information obtained from a crude oil assay.

TABLE 1

| Hydrocarbon Fraction | Boiling Point, °C. |
|---|---|
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

TABLE 2

| Property | Unit | Property Type | Fraction |
|---|---|---|---|
| Yield Weight and Volume % | Weight % and Volume % | Yield | All |
| API Gravity | API Gravity Degrees (° API) | Physical | All |
| Viscosity Kinematic (v) @ 38° C. | N/A | Physical | Fraction boiling >250° C. |
| Refractive Index @ 20° C. | N/A | Physical | Fraction boiling <400° C. |
| Sulfur | Weight % | Composition | All |
| Thiols/Mercaptans | Weight % | Composition | Fraction boiling <250° C. |
| Nickel | Weight % or ppm | Composition | Fraction boiling >400° C. |
| Nitrogen | Weight % or ppm | Composition | All |
| Flash Point, Cleveland open cup (COC) method | ° C. | Indicative | All |
| Cloud Point | ° C. | Indicative | Fraction boiling >250° C. |
| (Upper) Pour Point | ° C. | Indicative | Fraction boiling >250° C. |
| Freezing Point | ° C. | Indicative | Fraction boiling >250° C. |
| Microcarbon Residue | Weight % | Indicative | Fraction boiling >300° C. |
| Smoke Point | Millimeters (mm) | Indicative | Fraction boiling between 150° C.-250° C. |
| Octane Number | N/A | Indicative | Fraction boiling <250° C. |
| Cetane Index | N/A | Indicative | Fraction boiling between 150° C.-400° C. |
| Aniline Point | ° C. | Indicative | Fraction boiling <520° C. |

In various embodiments, the methods disclosed herein may advantageously eliminate the need for time consuming crude oil distillations and/or fractionations, while further simplifying a crude oil analysis through significant reductions in the required sample size volume. For example, the methods described herein may be performed on crude oil sample sizes as small as 1 milliliter (ml) to rapidly determine the properties of the crude oil sample as well as the properties various fractions thereof. In various embodiments, the fractions may include naphtha and diesel/gas oil fractions. In addition, the various embodiments disclosed herein may not require heating and/or cooling of a crude oil for the purpose of determining various properties of the crude oil or fractions thereof. Such properties may include cloud point (typically obtained using ASTM D2500), pour point (typically determined using ASTM D97) and aniline point (typically determined using ASTM D611).

In various embodiments, selected properties of a crude oil or fraction thereof may be determined using the methods disclosed herein. The selected properties may be determined advantageously without the cost and time associated with separation methods, such as distillation and/or fractionation, performed on a crude oil to obtain selected fractions of the crude oil for various testing methods. For example, cetane number, pour point, cloud point, and aniline point may be determined using the methods herein for a gas oil fraction of a crude oil without the need to separate the gas oil fraction from the crude oil via separation methods. As another example, the aromatic weight percentage of a gas oil fraction of a crude oil may be determined using the methods herein without the need to separate the aromatic fraction via separation methods or using an ASTM test or related test. As another example, the octane number of a naphtha fraction of a crude oil may be determined using the methods herein without the need to separate the naphtha fraction from the crude oil via separation methods.

The methodologies and techniques of the various embodiments disclosed herein advantageously may reduce the sample size, time, cost, and effort associated with evaluating one or more crude oils and fractions of crude oils through the spectroscopic and analytical techniques described herein. For instance, the time required to analyze crude oil samples (analysis time) using various embodiments may be reduced by 20%-100%. In various embodiments, the analysis time may be reduced by at least 25%. In various embodiments, the analysis time may be reduced by at least 50%. In various embodiments, the analysis time may be reduced by 25%-75%. In various embodiments, the analysis time may be reduced by 30-50%. The analysis time reduction is a reduction as compared to presently available assays and methods.

FIG. 1 schematically illustrates a method 100 for determining a property of a crude oil sample using a correlation of the property to a spectrum index and a density, in accordance with various embodiments. In various embodiments, the method 100 may be practiced in a computing device such as a personal computer, laptop computer, handheld or mobile computing device, or any type of computing device.

At 102 of the method 100, the method 100 may include obtaining a value of a property of a plurality of crude oils using a standard analysis method. In various embodiments, standard analysis methods may include various ASTM methods for testing crude oil and petroleum related products. In various embodiments, the property may be selected from the group consisting of cetane number, pour point, cloud point, and aniline point of a gas oil fraction, octane number of a naphtha fraction, and aromatic content of a gas oil fraction of a crude oil. In various embodiments, the gas oil fraction may have a boiling point range of approximately 180 to 370° C. In various embodiments, the naphtha fraction may have a boiling point of approximately 36 to 180° C. In various embodiments, the value of the cetane number may be obtained using ASTM D613. In various embodiments, the value of the pour point may be obtained using ASTM D7346, In various embodiments, the value of the cloud point may be obtained using ASTM D2500. In various embodiments, the value of the aniline point may be obtained using ASTM D611. In various embodiments, the value of the octane number may be obtained using at least one of a test for a motor octane, a research octane, and combinations thereof, wherein a value for the motor octane is obtain using ASTM D2700 and a value for the research octane is obtained using ASTM D2699. In various embodiments, the value of the aromatic content may be obtained using any suitable ASTM test or other test.

At 104 of the method 100, the method 100 may include obtaining a value of a density of the plurality of crude oils. In various embodiments, the value of the density may be obtained using ASTM D5002. The value of the density may be expressed in any units, including but not limited to units commonly used in the petroleum industry.

At 106 of the method 100, the method 100 may include obtaining data sets of scatter spectra for the plurality of crude oils. In various embodiments, the scatter spectra may be obtained using a laser induced ultraviolet (UV) fluorescence spectrometer, as further described herein and shown in FIGS. 2 and 3. In various embodiments, the scatter spectra may be obtained using a spectroscopy method selected from the group consisting of absorption spectroscopy, Raman spectroscopy, resonance Raman spectroscopy, transmission spectroscopy, ultraviolet-visible reflectance spectroscopy, and combinations thereof.

At 108 of the method 100, the method 100 may include calculating spectra indexes from the data sets of the scatter spectra of the plurality of crude oils. In various embodiments, the spectra indexes from the scatter spectra of the plurality of crude oils may be calculated from an indicative value of an area under a plot of fluorescence intensity versus a wavelength of UV light detected by a UV detector of the laser induced UV fluorescence spectrometer. In various embodiments, the indicative value (IN) of an area may be calculated using the equation $$IN = \sum_{\omega=\omega 1}^{\omega 2} \frac{FI_\omega}{10^6},$$

wherein FI is fluorescence intensity, $\omega$ is wavelength of UV light, $\omega 1$ is a beginning wavelength of UV light, and $\omega 2$ is an ending wavelength of UV light, wherein the beginning and ending wavelength of UV light may be selected to be at FI values greater than background noise of FI. In various embodiments, an arbitrary beginning and ending wavelength may be selected for the summation equation. In various embodiments, the indicative value of an area may be calculated by integrating the area under the plot of fluorescence intensity (FI) versus a wavelength of UV light detected by a UV detector of the laser induced UV fluorescence spectrometer from a beginning wavelength of UV light to an ending wavelength of UV light, wherein the beginning and ending wavelengths of UV light are selected to be at FI values greater than background noise of the FI. In various embodiments, an arbitrary beginning and ending wavelength may be selected for summation and/or integration.

At 110 of the method 100, the method 100 may include determining constants of a polynomial equation for the property, wherein the polynomial equation is a function of crude oil density and crude oil spectrum index, wherein the number of constants of the polynomial equation is equal to or less than the number of the plurality of crude oils, wherein the constants may be determined using a fitting method to fit the value of the property for the plurality of crude oils to a calculated value from the polynomial equation. In various embodiments, a least squares method may be used to determine the constants. In various embodiments, a regression method maybe used to determine the constants. In various embodiments, the polynomial equation may be $PROP=K+X_1*D+X_2*D^2+X_3*D^3+X_4*FI+X_5*FI^2+X_6*FI^3+*D*FI$, wherein PROP is a calculated value of the property, K and $X_i$ are constants specific to the respective property where i=1-7, D is density, and FI is spectrum index. In various embodiments, the number of constants may be eight, and the number of the plurality of crude oils may be nine.

At 112 of the method 100, the method 100 may include obtaining a scatter spectrum and a density of an uncharacterized crude oil sample and calculating spectrum index and a value of the property of the uncharacterized crude oil sample using the polynomial equation, wherein the uncharacterized crude oil sample is not one of the plurality of crude oils.

Figure 2:
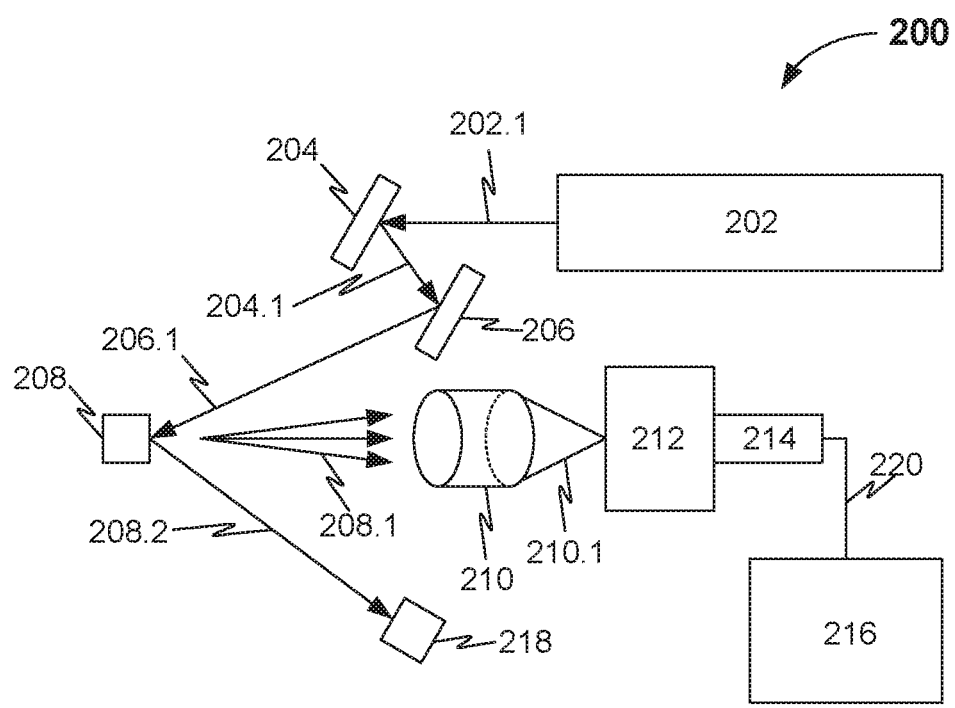
FIG. 2 schematically illustrates a rendering for a laser induced, ultraviolet (UV) fluorescence spectroscopy experimental setup, in accordance with various embodiments.

FIG. 2 schematically illustrates a laser induced ultraviolet (UV) fluorescence spectroscopy system 200, in accordance with various embodiments. The system 200 may include a laser 202 to emit a laser light 202.1. The system 200 may include a first mirror 204 to direct the laser light 202.1 off from the first mirror 204 to provide a first reflected light 204.1 to a second mirror 206. The second mirror 206 may reflect the first reflected light 204.1 to provide a second reflected light 206.1 to a cuvette 208 with a crude oil sample therein. The crude oil sample in cuvette 208 may emit fluorescent light 208.1 that may be directed towards lens system 210, which may provide a focused fluorescent light 210.1 to a spectrograph 212. The spectrograph 212 may be coupled to an intensified charge-coupled device (ICCD) 214. The ICCD 214 may be coupled 220 to a computer system 216 to record UV fluorescence spectrographic data from a sample in cuvette 208. The system 200 may include a beam dump 218 to receive reflected light 208.2.

The cuvette 208 may include four rectangular windows or sides and may be a standard UV quartz cuvette. The cuvette 208 may be sized to receive a sample of crude oil of approximately 2 milliliters. The first mirror 204, second mirror 206 and cuvette 208 may be configured to provide second reflected light 206.1 at approximately a 45 degree angle to a side of the cuvette 208.

The laser 202 may provide laser light 202.1 as a Q-switched UV laser beam at a wavelength of approximately 266 nm at beam diameter of approximately 0.5 mm. The Q-switching in the laser 202 may produce energetic pulses of approximately 35 millijoules per pulse for a period of 6 nanoseconds for each pulse. Other wavelengths of laser light may be used to induce a fluorescence response from a sample in cuvette 208. Laser light may have higher or lower energetic pulses and may have longer or shorter pulses.

Lens system 210 may include two or more quartz lenses aligned to focus the fluorescent emission 208.1 onto an entrance slit of spectrograph 212. The ICCD may be a fast-gated ICCD and may produce emission spectra of the resulting fluorescence intensity as function of wavelength. The resulting fluorescence spectra may have a resolution of approximately 1.5 nm. The spectra may be reconstructed using simulation software in computer system 216.

Figure 3:
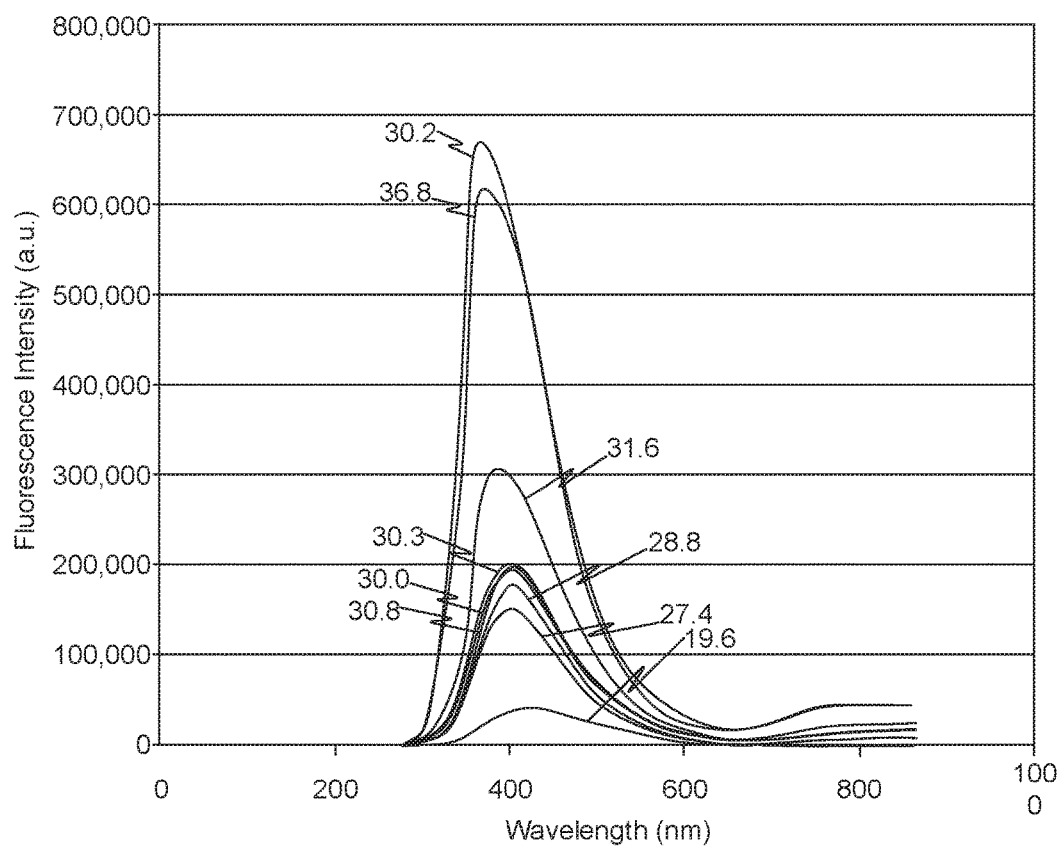
FIG. 3 schematically illustrates a laser-induced UV fluorescence spectra for crude oil samples with different American Petroleum Institute (API) gravity values.

FIG. 3 schematically illustrates a laser-induced UV fluorescence spectra for nine different crude oil samples with different American Petroleum Institute (API) gravity values, in accordance with various embodiments. Each spectra is labeled with the respective API gravity value. The spectra are shown as plots of fluorescence intensity (arbitrary units, a.u.) versus the wavelength (nanometers, nm).

In various embodiments, a laser induced UV fluorescence index ("IN") may be calculated from the spectra of a crude oil, as illustrated in FIG. 2. In various embodiments, IN may be calculated according to Equation 1 below.

$$IN = \sum_{\omega=\omega 1}^{\omega 2} \frac{FI_\omega}{10^6}$$ [Equation 1]

IN is a measure of fluorescence intensity at wavelength $\omega$. In various embodiments, fluorescence intensity may be measured in relative fluorescence units (RFU). In various embodiments, RFU may be measured as the fluorescence intensity values of a crude oil sample for peaks detected starting at $\omega$ equal to $\omega 1$ and up to $\omega$ equal to $\omega 2$. In various embodiments, $\omega 1$ may be approximately 283 nanometers, and $\omega 2$ may be approximately 600 nm. In various embodiments, IN may be calculated as the area under the curve for a plot of a measure of the fluorescence intensity, such as RFU for example, versus the wavelength of light detected by a detector. The area under the curve may be calculated according to Equation 1 or may be calculated using any suitable method to estimate the area under the curve. The starting wavelength $\omega 1$ and the ending wavelength $\omega 2$ may be optimized to provide improved accuracy in the calculation of IN for purposes of estimating properties of a hydrocarbon fraction or crude oil. For example $\omega 1$ may be from about 270 nm or lower to about 300 nm or higher. Similarly, $\omega 2$ may be from about 550 nm or lower to about 620 nm or higher. In various embodiments, $\omega$ may be incremented by 1 nm in Equation 1. In various embodiments, $\omega$ may be incremented by 1.5 nm in Equation 1. Any reasonable measure of the area under the curve may be used to calculate/estimate a value of IN, within reasonable engineering tolerances. In various embodiments, the value of IN may be a normalized value, where the normalized value may be with respect to a standard sample. Normalization may allow for comparison of index values from different fluorescence spectrometers. In various embodiments, a normalized IN may be used where IN is designated.

In various embodiments, IN may be combined with the density ("D") of a crude oil in a polynomial equation with eight constants in the equation to provide a means for determining a selected property ("PROP") of a crude oil. The constants of the equation may be determined by measuring IN, D, and PROP of at least eight different crude oils and performing a regression analysis or a least squares analysis of the data to determine the eight constants. Any standard fitting technique may be used to determine the eight constants. In various embodiments, polynomials with more than eight constants may be used. In various embodiments, polynomials with less than eight constants may be used.

In various embodiments, a polynomial equation may have the form shown in Equation 2.

$$PROP = K_{PROP} + X_{1PROP}*D + X_{2PROP}*D^2 + X_{3PROP}*D^3 + X_{4PROP}*IN + X_{5PROP}*IN^2 + X_{6PROP}*IN^3 + X_{7PROP}*D*IN$$ [Equation 2]

In various embodiments, PROP may be cetane number, pour point, cloud point, aniline point, octane, or weight percentage aromatics. If PROP, D, and IN are determined for at least eight different crude oils and/or fractions thereof, then the constants of Equation 2 may be determined. In various embodiments, IN may be a normalized IN to allow normalization with respect to various fluorescence spectrometers. In various embodiments, more than eight samples may be used to determine the constants of Equation 2. In such a case, a least squares analysis may be used to determine the constants since the system is overdetermined.

In various embodiments, cetane number (CN) may be determined for a crude oil fraction or sample using the methods described herein. In various embodiments, CN may be determined for a gas oil fraction boiling in the range of 180 to 370° C. using Equation 3 below.

$$CN = K_{CN} + X_{1CN}*D + X_{2CN}*D^2 + X_{3CN}*D^3 + X_{4CN}*IN + X_{5CN}*IN^2 + X_{6CN}*IN^3 + X_{7CN}*D*IN$$ [Equation 3]

In Equation 3, "$K_{CN}$" is a constant, and "$X_{nCN}$" are constants where the subscript n is 1, 2, ... 7.

In various embodiments, the constants $K_{CN}$ and $X_{nCN}$ may be determined via regression analysis of a database of crude oil data containing data for cetane, crude oil density, and IN.

In various embodiments, pour point (PP) may be determined for a crude oil fraction or sample using the methods described herein. In various embodiments, PP may be determined for a gas oil fraction boiling in the range of 180 to 370° C. using Equation 4 below.

$$PP = K_{PP} + X_{1PP}*D + X_{2PP}*D^2 + X_{3PP}*D^3 + X_{4PP}*IN + X_{5PP}*IN^2 + X_{6PP}*IN^3 + X_{7PP}*D*IN \quad \text{[Equation 4]}$$

In Equation 4, "$K_{PP}$" is a constant, and "$X_{nPP}$" are constants where the subscript n is 1, 2, ... 7. "D" and "IN" are as described previously.

In various embodiments, the constants $K_{PP}$ and $X_{nPP}$ may be determined via regression analysis of a database of crude oil data containing data for pour point, crude oil density, and IN.

In various embodiments, cloud point (CP) may be determined for a crude oil fraction or sample using the methods described herein. In various embodiments, CP may be determined for a gas oil fraction boiling in the range of 180 to 370° C. using Equation 5 below.

$$CP = K_{CP} + X_{1CP}*D + X_{2CP}*D^2 + X_{3CP}*D^3 X_{4CP}*IN + X_{5CP}*IN^2 + X_{6CP}*IN^3 + X_{7CP}*D*IN \quad \text{[Equation 5]}$$

In Equation 5, "$K_{CP}$" is a constant, and "$X_{nCP}$" are constants where the subscript n is 1, 2, ... 7. "D" and "IN" are as described previously.

In various embodiments, the constants $K_{CP}$ and $X_{nCP}$ may be determined via regression analysis of a database of crude oil data containing data for cloud point, crude oil density, and IN.

In various embodiments, aniline point (AP) may be determined for a crude oil fraction or sample using the methods described herein. In various embodiments, AP may be determined for a gas oil fraction boiling in the range of 180 to 370° C. using Equation 6 below.

$$AP = K_{AP} X_{1AP}*D + X_{2AP}*D^2 + X_{3AP}*D^3 + X_{4AP}*IN + X_{5AP}*IN^2 + X_{6AP}*IN^3 X_{7AP}*D*IN \quad \text{[Equation 6]}$$

In Equation 6, "$K_{AP}$" is a constant, and "$X_{nAP}$" are constants where the subscript n is 1, 2, ... 7. "D" and "IN" are as described previously.

In various embodiments, the constants $K_{AP}$ and $X_{nAP}$ may be determined via regression analysis of a database of crude oil data containing data for aniline, crude oil density, and IN.

In various embodiments, a weight percentage of aromatics (AR) may be determined for a gas oil fraction of a crude oil using the methods described herein. In various embodiments, AR may be determined using Equation 7 below.

$$AR = K_{AR} X_{1AR}*D + X_{2AR}*D^2 X_{3AR}*D^3 X_{4AR}*IN + X_{5AR}*IN^2 + X_{6AR}*IN^3 + X_{7AR}*D*IN \quad \text{[Equation 7]}$$

In Equation 7, "$K_{AR}$" is a constant, and "$X_{nAR}$" are constants where the subscript n is 1, 2, ... 7. "D" and "IN" are as described previously.

In various embodiments, the constants $K_{AR}$ and $X_{nAR}$ may be determined via regression analysis of a database of crude oil data containing data for aromatics percentage, crude oil density, and IN.

In various embodiments, the methods described herein may be used to determine an octane number (ON) for a naphtha fraction of a crude oil. In various embodiments, ON may be determined for a naphtha fraction having a boiling temperature of approximately 36 to 180° C. using Equation 8 below.

$$ON = K_{ON} + X_{1ON}*D + X_{2ON}*D^2 + X_{3ON}*D^3 + X_{4ON}*IN + X_{5ON}*IN^2 + X_{6ON}*IN^3 + X_{7ON}*D*IN \quad \text{[Equation 8]}$$

In Equation 8, "$K_{ON}$" is a constant, and "$X_{nON}$" are constants where the subscript n is 1, 2, ... 7. In various embodiments, $X_{nON}$ may be set to zero. "D" and "IN" are as described previously.

In various embodiments, the constants $K_{ON}$ and $X_{nON}$ may be determined via regression analysis of a database of crude oil data containing data for octane number, crude oil density, and IN.

EXAMPLES

According to various embodiments, the present disclosure describes methods and systems for determining properties of crude oil and/or fractions thereof from fluorescence spectroscopy data and crude oil density using a polynomial equation, as illustrated and described herein for the various embodiments.

In a further example of spectroscopic measurements of crude oil samples, fluorescence measurements were performed using the laser induced, ultraviolet (UV) fluorescence spectroscopy experimental system illustrated in FIG. 2. In this example, a 2 ml aliquot from selected crude oil samples were transferred to a standard UV quartz cuvette with four (4) rectangular windows or sides. The cuvette and aliquot were inserted into the spectrometer cell holder at an angle such that the incident laser beam is focused onto one of the (4) cuvette windows at a fixed angle of approximately 45 degrees for the duration of the experiment. A Q-switched UV laser beam at an initially fixed wavelength of 266 nanometers (nm) and a fixed beam diameter of about 0.5 mm was used to excite the crude oil aliquot within the cuvette. The Q-switching in the laser produced energetic pulses of about 35 millijoules (mJ) per pulse with a temporal span of about 6 nanoseconds (ns) for each pulse. The resulting fluorescence of for each of the crude oil samples was collected using a combination of quartz lenses aligned for focusing the resulting emission onto the entrance slit of an operably connected spectrograph, as illustrated by and described herein for FIG. 2. The spectrograph was coupled with a fast-gated intensified charge-coupled device (ICCD) to produce emission spectra of the resulting fluorescence intensity as function of wavelength. The spectral resolution was about 1.5 nm, and the spectra were reconstructed using simulation software. The ICCD was initiated by the "Q-switching" of the laser pulse, and the detection of the resulting fluorescence signal was limited to the first six nanoseconds as measured from the start from the maximal value of the laser pulse intensity. FIG. 2 illustrates the fluorescence spectra for nine different crude oils with differing API gravity values.

As illustrated in Table 3, the values produced from the above described spectral analysis may be used to determine a cetane number of a gas oil fraction of a crude oil. The gas oil fraction has a boiling point range of 180 to 370° C. The crude oil has a density of 0.883 g/cm$^3$. The calculated cetane number for the gas oil fraction of the crude oil is 59. The values for the eight constants shown in Table 3 were obtain by regression analysis of a data base of crude oil data.

TABLE 3

| Constant | Value of Constant | Equation Variables | Calculated Value of Variables | Equation | Calculated Value |
|---|---|---|---|---|---|
| $K_{PROP}$ | 3.2602035E+06 | | | $K_{PROP}$ | 3.260E+06 |
| $X_{1PROP}$ | -1.0883141E+07 | D | 8.8280E-01 | $X_{1PROP} * D$ | -9.608E+06 |
| $X_{2PROP}$ | 1.2107974E+07 | $D^2$ | 7.7934E-01 | $X_{2PROP} * D^2$ | 9.436E+06 |
| $X_{3PROP}$ | -4.4899405E+06 | $D^3$ | 6.8800E-01 | $X_{3PROP} * D^3$ | -3.089E+06 |
| $X_{4PROP}$ | -2.1896189E+03 | IN | 2.3377E+00 | $X_{4PROP} * IN$ | -5.119E+03 |
| $X_{5PROP}$ | -5.5692267E+01 | $IN^2$ | 5.4649E+00 | $X_{5PROP} * IN^2$ | -3.044E+02 |
| $X_{6PROP}$ | 3.6121466E+00 | $IN^3$ | 1.2775E+01 | $X_{6PROP} * IN^3$ | 4.615E+01 |
| $X_{7PROP}$ | 2.7911195E+03 | D * IN | 2.0637E+00 | $X_{7PROP} * D * IN$ | 5.760E+03 |
| PROP = CN | | | | | 59 |

As illustrated in Table 4, the values produced from the above described spectral analysis may be used to determine a pour point of a gas oil fraction of a crude oil. The gas oil fraction has a boiling point range of 180 to 370° C. The crude oil has a density of 0.883 g/cm³. The calculated pour point for the gas oil fraction of the crude oil is -10. The values for the eight constants shown in Table 4 were obtain by regression analysis of a data base of crude oil data.

TABLE 4

| Constant | Value of Constant | Equation Variables | Calculated Value of Variables | Equation | Calculated Value |
|---|---|---|---|---|---|
| $K_{PROP}$ | 3.4822532E+06 | | | $K_{PROP}$ | 3.482E+06 |
| $X_{1PROP}$ | -1.1630086E+07 | D | 8.8280E-01 | $X_{1PROP} * D$ | -1.027E+07 |
| $X_{2PROP}$ | 1.2945056E+07 | $D^2$ | 7.7934E-01 | $X_{2PROP} * D^2$ | 1.009E+07 |
| $X_{3PROP}$ | -4.8026139E+06 | $D^3$ | 6.8800E-01 | $X_{3PROP} * D^3$ | -3.304E+06 |
| $X_{4PROP}$ | -2.3031567E+03 | IN | 2.3377E+00 | $X_{4PROP} * IN$ | -5.384E+03 |
| $X_{5PROP}$ | -5.9091109E+01 | $IN^2$ | 5.4649E+00 | $X_{5PROP} * IN^2$ | -3.229E+02 |
| $X_{6PROP}$ | 3.7964428E+00 | $IN^3$ | 1.2775E+01 | $X_{6PROP} * IN^3$ | 4.850E+01 |
| $X_{7PROP}$ | 2.9444430E+03 | D * IN | 2.0637E+00 | $X_{7PROP} * D * IN$ | 6.077E+03 |
| PROP = PP | | | | | -10 |

As illustrated in Table 5, the values produced from the above described spectral analysis may be used to determine a cloud point of a gas oil fraction of a crude oil. The gas oil fraction has a boiling point range of 180 to 370° C. The crude oil has a density of 0.883 g/cm³. The calculated cloud point for the gas oil fraction of the crude oil is -8. The values for the eight constants shown in Table 5 were obtain by regression analysis of a data base of crude oil data.

TABLE 5

| Constant | Value of Constant | Equation Variables | Calculated Value of Variables | Equation | Calculated Value |
|---|---|---|---|---|---|
| $K_{PROP}$ | -1.5005814E+05 | | | $K_{PROP}$ | -1.501E+05 |
| $X_{1PROP}$ | 4.8804226E+05 | D | 8.8280E-01 | $X_{1PROP} * D$ | 4.308E+05 |
| $X_{2PROP}$ | -5.2926304E+05 | $D^2$ | 7.7934E-01 | $X_{2PROP} * D^2$ | -4.125E+05 |
| $X_{3PROP}$ | 1.9132056E+05 | $D^3$ | 6.8800E-01 | $X_{3PROP} * D^3$ | 1.316E+05 |
| $X_{4PROP}$ | 3.3467280E+02 | IN | 2.3377E+00 | $X_{4PROP} * IN$ | 7.824E+02 |
| $X_{5PROP}$ | -9.2521779E+00 | $IN^2$ | 5.4649E+00 | $X_{5PROP} * IN^2$ | -5.056E+01 |
| $X_{6PROP}$ | 5.9752663E-01 | $IN^3$ | 1.2775E+01 | $X_{6PROP} * IN^3$ | 7.634E+00 |
| $X_{7PROP}$ | -3.3414746E+02 | D * IN | 2.0637E+00 | $X_{7PROP} * D * IN$ | -6.896E+02 |
| PROP = CP | | | | | -10 |

As illustrated in Table 6, the values produced from the above described spectral analysis may be used to determine an aniline point of a gas oil fraction of a crude oil. The gas oil fraction has a boiling point range of 180 to 370° C. The crude oil has a density of 0.883 g/cm³. The calculated aniline point for the gas oil fraction of the crude oil is 69. The values for the eight constants shown in Table 6 were obtain by regression analysis of a data base of crude oil data.

TABLE 6

| Constant | Value of Constant | Equation Variables | Calculated Value of Variables | Equation | Calculated Value |
|---|---|---|---|---|---|
| $K_{PROP}$ | 5.7433836E+05 | | | $K_{PROP}$ | 5.743E+05 |
| $X_{1PROP}$ | −1.9146342E+06 | D | 8.8280E−01 | $X_{1PROP} * D$ | −1.690E+06 |
| $X_{2PROP}$ | 2.1279463E+06 | $D^2$ | 7.7934E−01 | $X_{2PROP} * D^2$ | 1.658E+06 |
| $X_{3PROP}$ | −7.8843455E+05 | $D^3$ | 6.8800E−01 | $X_{3PROP} * D^3$ | −5.424E+05 |
| $X_{4PROP}$ | −4.5720242E+02 | IN | 2.3377E+00 | $X_{4PROP} * IN$ | −1.069E+03 |
| $X_{5PROP}$ | −3.0191516E+00 | $IN^2$ | 5.4649E+00 | $X_{5PROP} * IN^2$ | −1.650E+01 |
| $X_{6PROP}$ | 2.1027054E−01 | $IN^3$ | 1.2775E+01 | $X_{6PROP} * IN^3$ | 2.686E+00 |
| $X_{7PROP}$ | 5.3551594E+02 | D * IN | 2.0637E+00 | $X_{7PROP} * D * IN$ | 1.105E+03 |
| PROP = AP | | | | | 65 |

As illustrated in Table 7, the values produced from the above described spectral analysis may be used to determine an aromatic weight percentage of a crude oil. The crude oil has a density of 0.883 g/cm³. The values for the eight constants shown in Table 7 were obtain by regression analysis of a data base of crude oil data.

TABLE 7

| Constant | Value of Constant | Equation Variables | Calculated Value of Variables | Equation | Calculated Value |
|---|---|---|---|---|---|
| $K_{PROP}$ | −1.441827E+06 | | | $K_{PROP}$ | −1.442E+06 |
| $X_{1PROP}$ | 4.796847E+06 | D | 8.8280E−01 | $X_{1PROP} * D$ | 4.235E+06 |
| $X_{2PROP}$ | −5.320518E+06 | $D^2$ | 7.7934E−01 | $X_{2PROP} * D^2$ | −4.146E+06 |
| $X_{3PROP}$ | 1.967479E+06 | $D^3$ | 6.8800E−01 | $X_{3PROP} * D^3$ | 1.354E+06 |
| $X_{4PROP}$ | 1.088830E+03 | IN | 2.3377E+00 | $X_{4PROP} * IN$ | 2.545E+03 |
| $X_{5PROP}$ | −8.202033E+00 | $IN^2$ | 5.4649E+00 | $X_{5PROP} * IN^2$ | −4.482E+01 |
| $X_{6PROP}$ | 4.321777E−01 | $IN^3$ | 1.2775E+01 | $X_{6PROP} * IN^3$ | 5.521E+00 |
| $X_{7PROP}$ | −1.194831E+03 | D * IN | 2.0637E+00 | $X_{7PROP} * D * IN$ | −2.466E+03 |
| PROP = AR | | | | | 21 |

As illustrated in Table 8, the values produced from the above described spectral analysis may be used to determine an octane number of a naphtha fraction of a crude oil. The naphta fraction has a boiling point range of less than 250° C. The crude oil has a density of 0.883 g/cm³. The calculated octane number is 54. The values for the eight constants shown in Table 8 were obtain by regression analysis of a data base of crude oil data.

TABLE 8

| Constant | Value of Constant | Equation Variables | Calculated Value of Variables | Equation | Calculated Value |
|---|---|---|---|---|---|
| $K_{PROP}$ | −1.3901183E+07 | | | $K_{PROP}$ | −1.390E+07 |
| $X_{1PROP}$ | 4.8611994E+07 | D | 8.8280E−01 | $X_{1PROP} * D$ | 4.291E+07 |
| $X_{2PROP}$ | −5.6657335E+07 | $D^2$ | 7.7934E−01 | $X_{2PROP} * D^2$ | −4.416E+07 |
| $X_{3PROP}$ | 2.2002750E+07 | $D^3$ | 6.8800E−01 | $X_{3PROP} * D^3$ | 1.514E+07 |
| $X_{4PROP}$ | 3.0362362E+03 | IN | 2.3377E+00 | $X_{4PROP} * IN$ | 7.098E+03 |
| $X_{5PROP}$ | −7.1327482E+02 | $IN^2$ | 5.4649E+00 | $X_{5PROP} * IN^2$ | −3.898E+03 |
| $X_{6PROP}$ | 4.8525799E+01 | $IN^3$ | 1.2775E+01 | $X_{6PROP} * IN^3$ | 6.199E+02 |
| $X_{7PROP}$ | — | D * IN | — | $X_{7PROP} * D * IN$ | — |
| PROP = ON | | | | | 54 |

Table 9 illustrates spectral analysis and wave number values for two crude oil samples with API indices of 28.8° and 27.4°, respectively.

TABLE 9

| Wavelength, nm | Crude 1 API = 28.8° | Crude 2 API = 27.4° |
|---|---|---|
| 283 | 2533 | 2229 |
| 284 | 1925 | 2293 |
| 285 | 1589 | 2374 |
| 286 | 2071 | 1399 |
| 287 | 2172 | 2207 |
| 288 | 1700 | 1404 |
| 289 | 1723 | 1964 |
| 290 | 2313 | 2239 |
| 291 | 2827 | 2377 |
| 292 | 2569 | 2453 |
| 293 | 2349 | 2642 |
| 294 | 2045 | 2846 |
| 295 | 2217 | 2606 |
| 296 | 2518 | 2329 |
| 297 | 2562 | 2931 |
| 298 | 3192 | 2671 |
| 299 | 2266 | 3072 |
| 300 | 2793 | 3150 |
| 301 | 3258 | 2870 |
| 302 | 3380 | 3608 |
| 303 | 3392 | 2926 |
| 304 | 4057 | 3869 |
| 305 | 3807 | 4037 |
| 306 | 4922 | 3491 |
| 307 | 4492 | 4142 |
| 308 | 4756 | 4854 |
| 309 | 5290 | 5550 |
| 310 | 6172 | 5533 |
| 311 | 6671 | 5810 |
| 312 | 6638 | 7132 |
| 313 | 7615 | 7116 |
| 314 | 8154 | 8055 |
| 315 | 9478 | 8862 |
| 316 | 10520 | 9888 |
| 317 | 10673 | 9935 |
| 318 | 12667 | 11124 |
| 319 | 12579 | 11623 |
| 320 | 13206 | 11909 |
| 321 | 13331 | 12847 |
| 322 | 15063 | 13990 |
| 323 | 14660 | 13843 |
| 324 | 16503 | 15107 |
| 325 | 16612 | 15758 |
| 326 | 17752 | 15864 |
| 327 | 18029 | 17237 |
| 328 | 19963 | 17993 |
| 329 | 18942 | 18623 |
| 330 | 21263 | 19318 |
| 331 | 22016 | 20085 |
| 332 | 23030 | 21060 |
| 333 | 24344 | 22203 |
| 334 | 24779 | 23990 |
| 335 | 27869 | 24203 |
| 336 | 28979 | 26844 |
| 337 | 30710 | 27792 |
| 338 | 32430 | 29174 |
| 339 | 35163 | 30955 |
| 340 | 35982 | 32703 |
| 341 | 38680 | 34904 |
| 342 | 41088 | 36602 |
| 343 | 42805 | 37940 |
| 344 | 45447 | 40355 |
| 345 | 46722 | 41923 |
| 346 | 48941 | 43950 |
| 347 | 51126 | 45384 |
| 348 | 52734 | 47401 |
| 349 | 55647 | 49629 |
| 350 | 57209 | 51362 |
| 351 | 60369 | 53357 |
| 352 | 62615 | 56110 |
| 353 | 64481 | 57903 |
| 354 | 67626 | 60018 |
| 355 | 71322 | 63831 |
| 356 | 74627 | 64889 |
| 357 | 77316 | 69261 |
| 358 | 82988 | 71863 |
| 359 | 86388 | 75262 |
| 360 | 90735 | 79052 |
| 361 | 94513 | 82015 |
| 362 | 99231 | 85314 |
| 363 | 103493 | 89486 |
| 364 | 107102 | 92245 |
| 365 | 111570 | 95020 |
| 366 | 115048 | 99540 |
| 367 | 118831 | 101792 |
| 368 | 121824 | 104330 |
| 369 | 126031 | 108308 |
| 370 | 128402 | 111153 |
| 371 | 131452 | 111854 |
| 372 | 134887 | 114664 |
| 373 | 136688 | 117067 |
| 374 | 139274 | 118927 |
| 375 | 143124 | 120944 |
| 376 | 145021 | 124053 |
| 377 | 148676 | 126957 |
| 378 | 150409 | 128167 |
| 379 | 154040 | 129882 |
| 380 | 153204 | 129377 |
| 381 | 158102 | 132376 |
| 382 | 160146 | 133499 |
| 383 | 161628 | 135191 |
| 384 | 162740 | 136106 |
| 385 | 164329 | 136516 |
| 386 | 166967 | 138932 |
| 387 | 167600 | 138682 |
| 388 | 168629 | 139413 |
| 389 | 170547 | 141818 |
| 390 | 171784 | 141954 |
| 391 | 171637 | 143307 |
| 392 | 171576 | 142213 |
| 393 | 173682 | 144258 |
| 394 | 174962 | 144150 |
| 395 | 176004 | 144783 |
| 396 | 176402 | 144994 |
| 397 | 176891 | 146836 |
| 398 | 177328 | 145306 |
| 399 | 179500 | 147283 |
| 400 | 177733 | 146605 |
| 401 | 178407 | 147255 |
| 402 | 179569 | 146905 |
| 403 | 179412 | 147258 |
| 404 | 178569 | 145785 |
| 405 | 179102 | 145864 |
| 406 | 180090 | 146780 |
| 407 | 179504 | 146764 |
| 408 | 180137 | 147206 |
| 409 | 180548 | 147712 |
| 410 | 180279 | 145875 |
| 411 | 178189 | 146376 |
| 412 | 178355 | 145693 |
| 413 | 177908 | 144959 |
| 414 | 177920 | 145348 |
| 415 | 176467 | 143386 |
| 416 | 175247 | 142439 |
| 417 | 174055 | 141745 |
| 418 | 173060 | 140886 |
| 419 | 172054 | 140424 |
| 420 | 170763 | 139331 |
| 421 | 170813 | 139233 |
| 422 | 170648 | 137928 |
| 423 | 169624 | 137084 |
| 424 | 168176 | 136467 |
| 425 | 166949 | 136398 |
| 426 | 166644 | 133006 |
| 427 | 163869 | 133064 |
| 428 | 164317 | 131752 |
| 429 | 162025 | 130243 |
| 430 | 160674 | 129345 |
| 431 | 157933 | 128243 |
| 432 | 156799 | 126119 |
| 433 | 155915 | 125234 |
| 434 | 154201 | 123712 |
| 435 | 153026 | 122139 |
| 436 | 150454 | 120476 |

TABLE 9-continued

| Wavelength, nm | Crude 1 API = 28.8° | Crude 2 API = 27.4° |
| --- | --- | --- |
| 437 | 149665 | 121200 |
| 438 | 147972 | 117146 |
| 439 | 145372 | 117156 |
| 440 | 144243 | 115651 |
| 441 | 142637 | 114614 |
| 442 | 140302 | 112923 |
| 443 | 139870 | 112657 |
| 444 | 136375 | 110729 |
| 445 | 134417 | 109654 |
| 446 | 133623 | 108739 |
| 447 | 131655 | 106128 |
| 448 | 128464 | 105405 |
| 449 | 128869 | 103827 |
| 450 | 126147 | 103553 |
| 451 | 122958 | 100621 |
| 452 | 123258 | 100068 |
| 453 | 122061 | 99447 |
| 454 | 119715 | 97214 |
| 455 | 118282 | 96916 |
| 456 | 116159 | 95221 |
| 457 | 115287 | 93529 |
| 458 | 113518 | 92666 |
| 459 | 112716 | 90743 |
| 460 | 110533 | 90317 |
| 461 | 109059 | 88090 |
| 462 | 107834 | 87533 |
| 463 | 106323 | 85673 |
| 464 | 104581 | 85672 |
| 465 | 102713 | 85115 |
| 466 | 102190 | 82367 |
| 467 | 99801 | 81123 |
| 468 | 98581 | 78631 |
| 469 | 97790 | 78260 |
| 470 | 95193 | 77702 |
| 471 | 94465 | 76745 |
| 472 | 93551 | 74711 |
| 473 | 91720 | 73368 |
| 474 | 90512 | 72131 |
| 475 | 89185 | 71357 |
| 476 | 88422 | 70099 |
| 477 | 85896 | 69086 |
| 478 | 84775 | 66851 |
| 479 | 83740 | 66305 |
| 480 | 82836 | 64634 |
| 481 | 81911 | 64422 |
| 482 | 79912 | 63023 |
| 483 | 78857 | 62187 |
| 484 | 77448 | 61551 |
| 485 | 75629 | 60649 |
| 486 | 75164 | 59332 |
| 487 | 73504 | 58507 |
| 488 | 71739 | 57484 |
| 489 | 71147 | 56114 |
| 490 | 70135 | 56417 |
| 491 | 68244 | 54197 |
| 492 | 66558 | 53631 |
| 493 | 66237 | 53251 |
| 494 | 65402 | 51506 |
| 495 | 64211 | 51252 |
| 496 | 62971 | 50307 |
| 497 | 62805 | 50311 |
| 498 | 60166 | 48948 |
| 499 | 60326 | 47763 |
| 500 | 58902 | 48382 |
| 501 | 58449 | 47019 |
| 502 | 57264 | 46520 |
| 503 | 56987 | 45045 |
| 504 | 54966 | 44836 |
| 505 | 54825 | 43605 |
| 506 | 53606 | 44116 |
| 507 | 53185 | 43465 |
| 508 | 52441 | 43223 |
| 509 | 50591 | 42191 |
| 510 | 50117 | 41409 |
| 511 | 49697 | 41753 |
| 512 | 49568 | 39984 |
| 513 | 48271 | 40072 |
| 514 | 46594 | 40180 |
| 515 | 47069 | 38387 |
| 516 | 46439 | 38799 |
| 517 | 45933 | 38061 |
| 518 | 45563 | 37166 |
| 519 | 44639 | 37552 |
| 520 | 43795 | 35530 |
| 521 | 43469 | 36095 |
| 522 | 42155 | 34608 |
| 523 | 41549 | 35288 |
| 524 | 41433 | 34523 |
| 525 | 40956 | 34450 |
| 526 | 41154 | 33983 |
| 527 | 39253 | 32692 |
| 528 | 39572 | 32549 |
| 529 | 38589 | 32494 |
| 530 | 38053 | 31150 |
| 531 | 37399 | 30990 |
| 532 | 37307 | 30365 |
| 533 | 36276 | 29987 |
| 534 | 36206 | 29108 |
| 535 | 35205 | 29010 |
| 536 | 35671 | 27902 |
| 537 | 34531 | 27992 |
| 538 | 33872 | 27682 |
| 539 | 32661 | 26913 |
| 540 | 33070 | 27293 |
| 541 | 32009 | 25699 |
| 542 | 32410 | 26547 |
| 543 | 31867 | 24609 |
| 544 | 30827 | 25235 |
| 545 | 30570 | 24767 |
| 546 | 29468 | 24579 |
| 547 | 29676 | 23983 |
| 548 | 28726 | 22972 |
| 549 | 28551 | 23391 |
| 550 | 28687 | 22437 |
| 551 | 26184 | 22018 |
| 552 | 26578 | 21354 |
| 553 | 26361 | 22029 |
| 554 | 26010 | 21208 |
| 555 | 26264 | 21250 |
| 556 | 25533 | 20620 |
| 557 | 24608 | 19632 |
| 558 | 24447 | 20363 |
| 559 | 23731 | 19959 |
| 560 | 22711 | 19174 |
| 561 | 22869 | 19055 |
| 562 | 22580 | 18517 |
| 563 | 21943 | 18354 |
| 564 | 22050 | 17319 |
| 565 | 21764 | 18330 |
| 566 | 21086 | 17434 |
| 567 | 20523 | 17671 |
| 568 | 20268 | 17219 |
| 569 | 19934 | 16644 |
| 570 | 20014 | 16466 |
| 571 | 19262 | 15710 |
| 572 | 19275 | 16133 |
| 573 | 18918 | 16207 |
| 574 | 18488 | 15825 |
| 575 | 18063 | 14875 |
| 576 | 17565 | 15556 |
| 577 | 17886 | 14514 |
| 578 | 17075 | 14491 |
| 579 | 17398 | 14068 |
| 580 | 16880 | 14073 |
| 581 | 16684 | 13834 |
| 582 | 16181 | 13910 |
| 583 | 16212 | 13654 |
| 584 | 15796 | 13218 |
| 585 | 15912 | 12442 |
| 586 | 14781 | 12830 |
| 587 | 15122 | 12453 |
| 588 | 14622 | 11690 |
| 589 | 14806 | 12087 |
| 590 | 14241 | 12307 |

TABLE 9-continued

| Wavelength, nm | Crude 1 API = 28.8° | Crude 2 API = 27.4° |
|---|---|---|
| 591 | 14741 | 11893 |
| 592 | 13257 | 11473 |
| 593 | 13324 | 11736 |
| 594 | 13039 | 11404 |
| 595 | 12060 | 10984 |
| 596 | 13535 | 10448 |
| 597 | 11781 | 10699 |
| 598 | 13597 | 9861 |
| 599 | 11106 | 9258 |
| 600 | 12336 | 10198 |

What is claimed is:

1. A method for determining a value of a select property of an uncharacterized crude oil sample, comprising:
   obtaining an uncharacterized crude oil sample, the sample being between one to two milliliters in volume and not subject to any fractionation,
   obtaining a plurality of values of the select property of a plurality of crude oils using a standard analysis method, the select property being selected from the group consisting of cetane number, pour point, cloud point, aniline point, and octane number of a crude oil, and the uncharacterized crude oil is not one of the plurality of crude oils;
   obtaining a plurality of values of density of the plurality of crude oils;
   obtaining a plurality of data sets of scatter spectra for the plurality of crude oils using a laser induced ultraviolet (UV) fluorescence spectrometer;
   calculating a plurality of laser induced UV fluorescence indexes for the plurality of crude oils from the plurality of data sets of the scatter spectra of the plurality of crude oils;
   obtaining a scatter spectrum of the uncharacterized crude oil sample using the laser induced UV fluorescence spectrometer;
   calculating a laser induced UV fluorescence index of the uncharacterized crude oil sample based on the scatter spectrum of the uncharacterized crude oil sample;
   determining constants of a polynomial equation to determine the value of the select property of the uncharacterized crude oil,
   the polynomial equation is a function of density and laser induced UV fluorescence index of the uncharacterized crude oil sample,
   a number of the constants of the polynomial equation is equal to or less than the number of the plurality of crude oils, and
   the constants of the polynomial equation are determined using a fitting method to fit the plurality of values of the select property of the plurality of crude oils to the plurality of values of the density of the plurality of crude oils and the plurality of laser induced UV fluorescence indexes for the plurality of crude oils; and
   calculating the value of the select property of the uncharacterized crude oil sample using the polynomial equation.

2. The method of claim 1, wherein the cetane number, the pour point, the cloud point, and the aniline point are properties of a gas oil fraction of the plurality of crude oils and the uncharacterized crude oil sample; and the gas oil fraction has a boiling point range of approximately 180 to 370° C.

3. The method of claim 1, wherein the octane number is a property of a naphtha fraction of the plurality of crude oils and the uncharacterized crude oil sample; and the naphtha fraction has a boiling point of approximately 36 to 180° C.

4. The method of claim 1, wherein the cetane number of the plurality of crude oils is obtained using ASTM D613.

5. The method of claim 1, wherein the pour point of the plurality of crude oils is obtained using ASTM D7346.

6. The method of claim 1, wherein the cloud point of the plurality of crude oils is obtained using ASTM D2500.

7. The method of claim 1, wherein the aniline point of the plurality of crude oils is obtained using ASTM D611.

8. The method of claim 1, wherein the octane number of the plurality of crude oils is obtained using at least one of a test for a motor octane, a research octane, and combinations thereof, wherein a value for the motor octane is obtain using ASTM D2700 and a value for the research octane is obtained using ASTM D2699.

9. The method of claim 1, wherein the density of the uncharacterized crude oil sample and the plurality of crude oils is obtained using ASTM D5002.

10. The method of claim 1, wherein the plurality of the laser induced UV fluorescence indexes from plurality of data sets of scatter spectra of the plurality of crude oils are calculated from an indicative value (IN) of an area under a plot of fluorescence intensity (FI) versus a wavelength of ultraviolet (UV) light detected by an ultraviolet detector of the laser induced UV fluorescence spectrometer.

11. The method of claim 10, wherein the IN of an area is calculated via IN=

$$IN = \sum_{\omega=\omega 1}^{\omega 2} \frac{FI_\omega}{10^6},$$

$\omega$ is wavelength of UV light, $\omega 1$ is a beginning wavelength of UV light, and $\omega 2$ is an ending wavelength of UV light, wherein the beginning and ending wavelength of UV light are selected to be at FI values greater than background noise of FI.

12. The method of claim 10, wherein the IN of an area is calculated by integrating the area under the plot of FI versus a wavelength of UV light detected by the UV detector of the laser induced UV fluorescence spectrometer from a beginning wavelength of UV light to an ending wavelength of UV light, wherein the beginning and ending wavelengths of UV light are selected to be at FI values greater than background noise of the FI.

13. The method of claim 1, wherein the polynomial equation is $PROP=K+X_1*D+X_2*D^2+X_3*D^3+X_4*IN+X_5*IN^2+X_6*IN^3+X_7*D*IN$, wherein PROP is a calculated value of the select property of the uncharacterized crude oil sample, K and $X_i$ are constants specific to the respective select property of the plurality of crude oils where i=1–7, D is density of the uncharacterized crude oil sample, and IN is spectrum index of the uncharacterized crude oil sample.

14. A method for determining quality of diesel in the uncharacterized crude oil sample, comprising:
   providing an uncharacterized crude oil sample without subjecting the uncharacterized crude oil sample to fractionation;
   obtaining a plurality of cetane number for a plurality of crude oils using a standard analysis method, wherein the uncharacterized crude oil sample is not one of the plurality of crude oils;

obtaining a plurality of values of density of the plurality of crude oils;

obtaining a plurality of data sets of scatter spectra for the plurality of crude oils using a laser induced ultraviolet (UV) fluorescence spectrometer;

calculating a plurality of laser induced UV fluorescence indexes for the plurality of crude oils from the plurality of data sets of the scatter spectra of the plurality of crude oils;

obtaining a scatter spectrum of the uncharacterized crude oil sample using the laser induced ultraviolet fluorescence spectrometer;

calculating a laser induced UV fluorescence index of the uncharacterized crude oil sample based on the scatter spectrum of the uncharacterized crude oil sample;

determining constants of a polynomial equation to determine the cetane number of the uncharacterized crude oil, wherein the polynomial equation is a function of density and the laser induced UV fluorescence index of the uncharacterized crude oil sample, a number of constants of the polynomial equation is equal to or less than the number of the plurality of crude oils, and the constants of the polynomial equation are determined using a fitting method to fit the plurality of cetane number for the plurality of crude oils to the plurality of values of the density of the plurality of crude oils and the plurality of laser induced UV fluorescence indexes for the plurality of crude oils; and determining quality of diesel in the uncharacterized crude oil sample in response to the cetane number of the uncharacterized crude oil.

15. The method of claim 14, where the uncharacterized crude oil sample is obtained from a downhole drilling operation and subjected to analysis in the laser induced ultraviolet fluorescence spectrometer.

* * * * *